US000001139H

United States Statutory Invention Registration [19]

[11] Reg. Number: H1139

Grover

[43] Published: Feb. 2, 1993

[54] COMBINATION OF A CALCIUM CHANNEL BLOCKER AND THROMBOXANE $A_2$ RECEPTOR ANTAGONIST OR SYNTHETASE INHIBITOR AND METHOD FOR TREATING ISCHEMIA EMPLOYING SUCH COMBINATION

[75] Inventor: Gary J. Grover, Stockton, N.J.

[73] Assignee: E. R. Squibb & Sons, Inc., Princeton, N.J.

[21] Appl. No.: 222,671

[22] Filed: Jul. 21, 1988

[51] Int. Cl.[5] ..... A01N 43/00; A61K 31/55

[52] U.S. Cl. ..... 514/211; 514/469

[58] Field of Search ..... 514/211, 469

[56] References Cited

U.S. PATENT DOCUMENTS 4,663,336 5/1987 Nakane et al. ..... 514/381

OTHER PUBLICATIONS

L. Szekeres et al, Br. J. Pharmacol. 86:341-350, 1985.
G. Grover et al, Eur. J. Pharmacol. 143:109-117, 197.
R. Conway et al, J. Clin. Invest. 70:320-329, 1982.
G. Grover et al, J. Cardiovasc. Pharmacol. 11:29-35, 1988.

*Primary Examiner*—Robert L. Stoll
*Assistant Examiner*—Joseph D. Anthony
*Attorney, Agent, or Firm*—Burton Rodney

[57] ABSTRACT

A method is provided for treating ischemia in a mammalian species by administering a combination of a calcium channel blocker such as diltiazem, SQ 31,765 or SQ 32,324 and a thromoboxane $A_2$ receptor antagonist such as SQ 30,741 or a thromboxane synthetase inhibitor such as dazoxiben.

11 Claims, 2 Drawing Sheets

Figure 1:
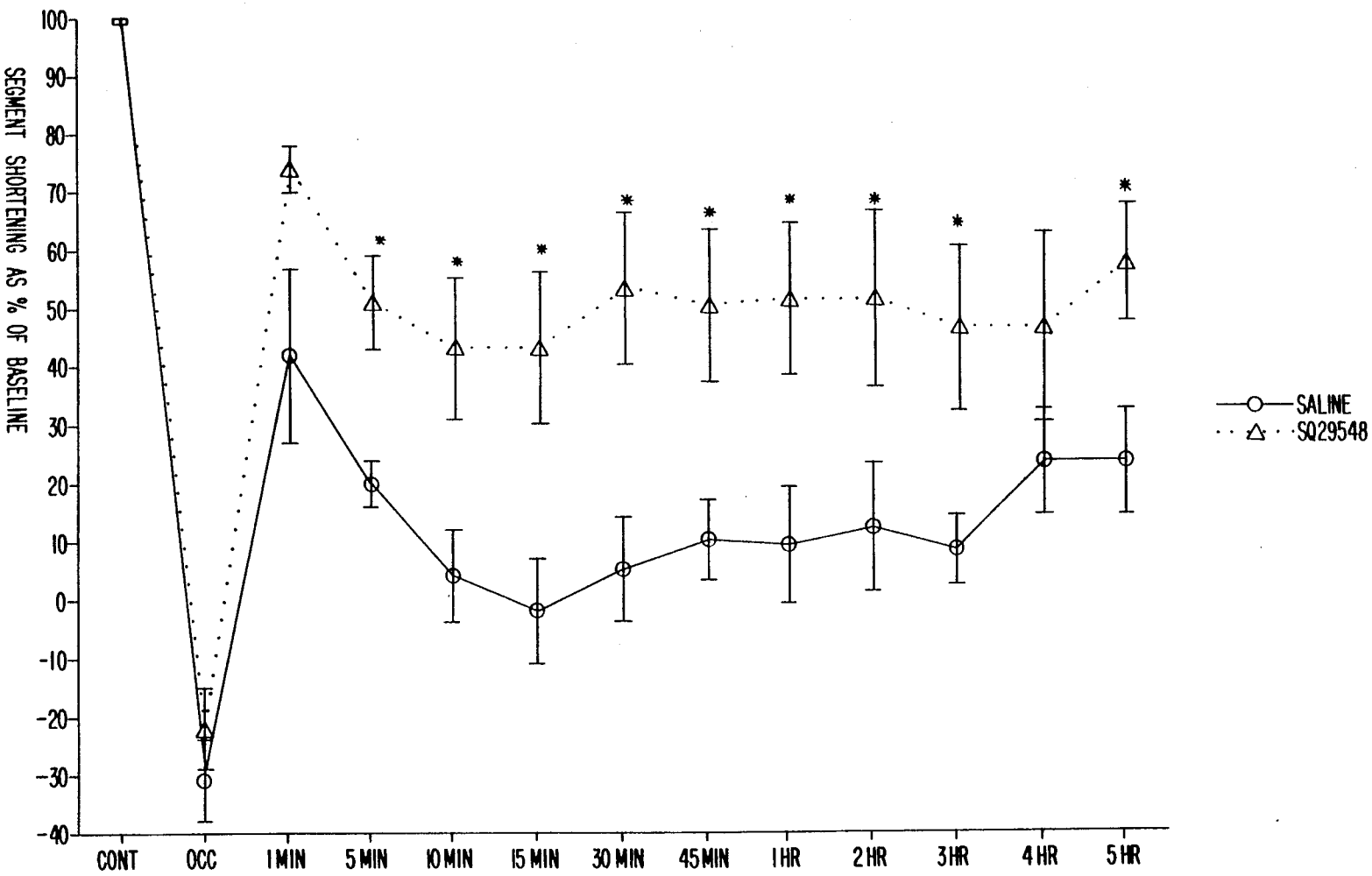

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

COMBINATION OF A CALCIUM CHANNEL BLOCKER AND THROMBOXANE $A_2$ RECEPTOR ANTAGONIST OR SYNTHETASE INHIBITOR AND METHOD FOR TREATING ISCHEMIA EMPLOYING SUCH COMBINATION

FIELD OF THE INVENTION

The present invention relates to a combination of a calcium channel blocker and a thromboxane $A_2$ receptor antagonist or thromboxane synthetase inhibitor and to a method for treating ischemia and/or reducing infarct size in mammalian species by administering such combination.

BACKGROUND OF THE INVENTION

There are several different classes of compounds which may have anti-ischemic properties under the right conditions. The mechanisms of action of many of these compounds are incompletely understood at best. Some of these compounds may act at different molecular sites, but ultimately may work via similar physiological mechanisms. Calcium antagonists are thought to be effective in reducing the severity of myocardial ischemia by their effects on reducing myocardial work as well as increasing blood flow to the ischemic region, Szekeres, L., et al., "Importance of myocardial flow changes in the protective action of diltiazem in a new model of myocardial ischemia." Br. J. Pharmacol 86:341–350, 1985; and Grover, G. and Parham, C. "The effect of diltiazem on ST-segment elevation and myocardial blood flow distribution during pacing-induced ischemia." Eur. J. Pharmacol 143:109–117, 1987. $\beta$-Adrenoceptor antagonists such as propranolol can also reduce the severity of an ischemic episode and this may also occur via their effect on work or flow, Conway, R. and Weiss, H., "Role of propranolol in improvement of the relationship between $O_2$ supply and consumption in an ischemic region of the dog heart." J. Clin. Invest. 70:320–329, 1982. Thus, one would not expect a combination of these two compounds to have additive effects above what one would expect from just increasing the dose of one or the other compound alone, unless other unknown protective mechanisms exist. One other problem is that combining these two classes of compounds may result in additive effects which may be contraindicated. An example would be the excessive hypotension and tachycardia which may be seen with $\beta$-blockers and calcium antagonists. This would be contraindicated in patients in the critical care setting where cardiac function may already be severely compromised. Thus, multiple drug treatment of myocardial ischemia may be best when drugs of differing physiological mechanisms of action are used.

Recently, it has been shown that thromboxane receptor antagonists possess potent anti-ischemic properties which appear to occur independently of changes in heart work or blood flow, Grover, G. and Schumacher, W., "Effect of the thromboxane receptor antagonist SQ 29,548 on myocardial infarct size in dogs." J. Cardiovasc. Pharmacol. 11:29–35, 1988. The appear to work via a mechanism different from the calcium antagonists or $\beta$-blockers.

DESCRIPTION OF THE INVENTION

In accordance with the present invention, a method is provided for treating ischemia in mammalian species over a prolonged period and/or reduce infarct size wherein a therapeutically effective amount of a calcium channel blocker in combination with a thromboxane $A_2$ receptor antagonist or thromboxane synthetase inhibitor is systemically, such as orally or parenterally, administered over a prolonged period.

In addition, in accordance with the present invention, a combination of a calcium channel blocker and a thromboxane $A_2$ receptor antagonist or a thromboxane synthetase inhibitor is provided wherein the calcium channel blocker is employed in a weight ratio to a thromboxane $A_2$ receptor antagonist or thromboxane synthetase inhibitor of within the range of from about 0.1:1 to about 10:1 and preferably from about 0.4:1 to about 2.5:1.

The term ischemia as employed herein refers to a reduction in blood flow such as cerebral ischemia, myocardial ischemia, ischemia in the limbs, and the like, such as caused by intermittent claudication, shock, trauma, hemorrhage, thromboses, clots and the like.

It has been found that the combination of the calcium channel blocker and thromboxane $A_2$ receptor antagonist or thromboxane synthetase inhibitor is a surprising and unique concept in treating ischemia in that it provides additional antiischemic effects over that which may be obtained using calcium channel blockers alone, such as reduced myocardial infarct size, prevention of reocclusion and reduction of angina pain without any additional adverse side effects, such as hypotension and tachycardia. In addition, the combination of the invention which includes compounds with different mechanisms of action, may be used to effectively treat ischemic heart disease of multiple etiology. One example may be unstable angina initiated by thrombus formation where thromboxane antagonists have been shown to have possible efficacy in inhibiting the thrombus formation (unlike calcium channel blockers) while the calcium channel blockers will combat the ischemia caused by the thrombus which is reducing flow in the coronaries. In this way, one would have a better chance of effecting improvements in these patients.

The calcium channel blocker also referred to as calcium entry blocker or calcium antagonist which is used herein is preferably diltiazem which is disclosed in U.S. Pat. No. 3,562,257 and which has the chemical name 3-(acetyloxy)-5-2-(dimethylamino)ethyl-2,3-dihydro-2-(4-methoxyphenyl)-1,5-benzothiazepin-4(5H)-one and the structure

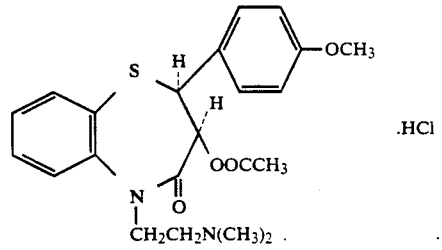

In addition, the calcium channel blocker may be a benzazepine derivative such as disclosed in U.S. patent application Ser. No. 42,187, filed Apr. 24, 1987, and which has the formula

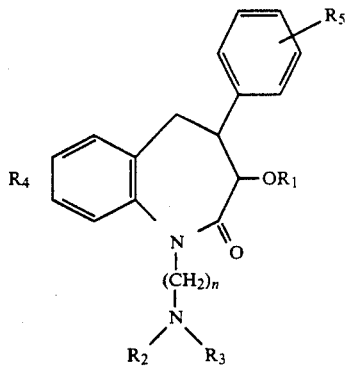

or a pharmaceutically acceptable salt thereof wherein $R_1$ is hydrogen, alkyl, alkanoyl, alkenyl, arylcarbonyl, heteroarylcarbonyl or $$-\overset{O}{\overset{\|}{C}}-NX_1X_2;$$

$R_2$ and $R_3$ are each independently hydrogen, alkyl, cycloalkyl or arylalkyl or $R_2$ and $R_3$ together with the nitrogen atom to which they are attached are pyrrolidinyl, piperidinyl, or morpholinyl;

$R_4$ and $R_5$ are each independently hydrogen, halogen, alkyl, alkoxy, aryloxy, arylalkoxy, diarylalkoxy, arylalkyl, cyano, hydroxy, alkanoyloxy, $$-O-\overset{O}{\overset{\|}{C}}-NX_1X_2,$$

fluoro substituted alkoxy, fluoro substituted alkyl, (cycloalkyl)alkoxy, $-NO_2$, $-NX_3X_4$, $-S(O)_m$alkyl, $-S(O)_m$aryl, $$-\overset{O}{\overset{\|}{C}}-X_5, \quad \text{or} \quad -O-\overset{O}{\overset{\|}{C}}-X_6;$$

n is 2 or 3;

m is 0, 1 or 2;

$X_1$ and $X_2$ are each independently hydrogen, alkyl, aryl or heteroaryl, or $X_1$ and $X_2$ together with the nitrogen atom to which they are attached are pyrrolidinyl, piperidinyl or morpholinyl;

$X_3$ and $X_4$ are each independently hydrogen, alkyl, alkanoyl, arylcarbonyl, heteroarylcarbonyl, or $$-\overset{O}{\overset{\|}{C}}-NX_1X_2;$$

$X_5$ is hydroxy, alkoxy, aryloxy, amino, alkylamino or dialkylamino; and $X_6$ is alkyl, alkoxy or aryloxy; with the proviso that if $R_4$ is a 7-alkyl group, it must have a tertiary carbon atom bonded to the ring;

wherein the term "aryl" refers to phenyl and phenyl substituted with 1, 2 or 3 amino, alkylamino, dialkylamino, nitro, halogen, hydroxyl, trifluoromethyl, alkyl of 1 to 4 carbon atoms, alkoxy of 1 to 4 carbon atoms, alkanoyloxy, carbamoyl, or carboxyl groups; and the term "heteroaryl" refers to pyridinyl, pyrrolyl, imidazolyl, furyl, thienyl, or thiazolyl.

A preferred such benzazepine derivative has the structure

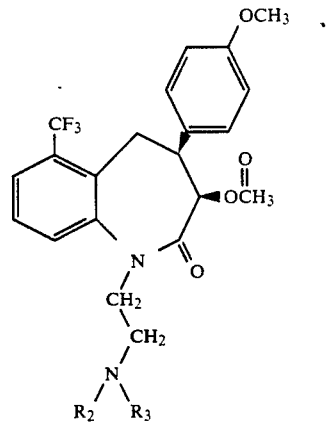

wherein $R_2$ and $R_3$ are each $CH_3$ or one of $R_2$ and $R_3$ is H and the other is $CH_3$, including the hydrochloride salts thereof.

Examples of other calcium channel blockers or calcium antagonists suitable for use herein include verapamil, tiapamil, 4-phenyl-1,4-dihydropyridines as defined hereinafter (including nifedipine) and the like.

4-Phenyl-1,4-dihydropyridine calcium antagonists which may be employed herein have the structure

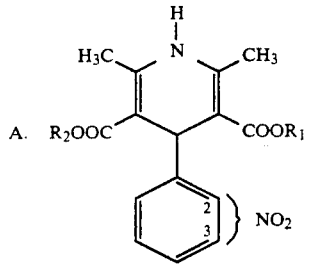

wherein $R_1$ and $R_2$ may be the same or different and are lower alkyl or lower alkoxy (lower alkyl) where lower alkyl and lower alkoxy contain 1 to 4 carbons.

The above compounds and methods for preparing same are disclosed in U.S. Pat. Nos. 3,644,627, 3,485,847, 3,488,359, 3,574,843, 3,799,934, 3,932,645 and 4,154,839 which are incorporated herein by reference.

The dihydropyridine calcium antagonist present in the beadlet composition of the invention will preferably be nifedipine, that is, the compound of formula A wherein $R_1$ is $CH_3$, $R_2$ is $CH_3$ and $NO_2$ is at the 2-position, namely, B. 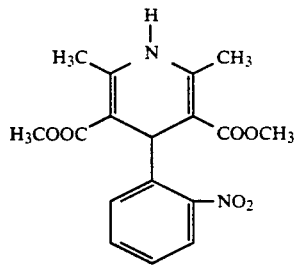

which is disclosed in U.S. Pat. Nos. 3,644,627 and 3,485,847.

Other preferred 4-phenyl-1,4-dihydropyridine calcium antagonists suitable for use herein include niludipine, that is, the compound of formula A wherein $R_1$ is $—(CH_2)_2OC_3H_7$, $R_2$ is $—(CH_2)_2OC_3H_7$ and $NO_2$ is at the 3-position (disclosed in U.S. Pat. Nos. 3,488,359 and 3,574,843); nimodipine, that is the compound of formula A wherein $R_1$ is $—(CH_2)_2OCH_3$, $R_2$ is $—CH(CH_3)_2$ and $NO_2$ is at the 3-position (disclosed in U.S. Pat. Nos. 3,799,934 and 3,932,645); nitrendipine, that is, the compound of formula A wherein $R_1$ is $—CH_2CH_3$, $R_2$ is $—CH_3$ and $NO_2$ is at the 3-position (disclosed in U.S. Pat. Nos. 3,799,934 and 3,932,645); and nisoldipine, that is, the compound of formula A wherein $R_1$ is $—CH_3$, $R_2$ is $—CH_2CH(CH_3)_2$ and $NO_2$ is at the 2-position (disclosed in U.S. Pat. Nos. 3,799,934, 3,932,645 and 4,154,839).

Other calcium channel blockers which may be employed herein include the benzothiazepine derivatives disclosed in U.S. Pat. No. 4,654,335 and U.S. Pat. No. 4,584,131, benzodiazepine derivatives disclosed in U.S. Pat. Nos. 4,650,797 and 4,647,561, and pyrimidine derivatives such as disclosed in U.S. Pat. Nos. 4,684,656, 4,689,414 and 4,684,655.

Thromboxane $A_2$ antagonists which may be employed herein include the 7-oxabicycloheptane and 7-oxabicycloheptene compounds disclosed in U.S. Pat. No. 4,537,981 to Snitman et al, especially, [1S-[1α,2β(5Z),3β(1E,3R,4S),4α]]-7 -[3-(3-hydroxy-4-phenyl-1-pentenyl)-7-oxabicyclo-[2.2.1]hept-2-yl]-5-heptenoic acid; the 7-oxabicycloheptane substituted aminoprostaglandin analogs disclosed in U.S. Pat. No. 4,416,896 to Nakane et al., especially, [1S-[1α,2β(5Z),3β,4α]]-7-[3-[[2-(phenylamino)carbonyl]hydrazino]methyl]-7-oxabicyclo[2.2.1]hept-2-yl]-5-heptenoic acid; the 7-oxabicycloheptane substituted diamide prostaglandin analogs disclosed in U.S. Pat. No. 4,663,336 to Nakane et al, especially, [1S-[1α,2β(5Z)-,3α,4β]]-7-[3-[[[[(1-oxoheptyl)amino]acetyl]amino]methyl]-7-oxabicyclo[2.2.1]-hept-2-yl]-5-heptenoic acid (SQ 30,471), which is preferred, and the corresponding tetrazole, and [1S-[1α,2β(Z),3α,4β]]-7-[3-[[[[(4-cyclohexyl-1-oxobutyl)amino]acetyl]amino]methyl]-7-oxabicyclo-[2.2.1]hept-2-yl]-5-heptenoic acid; the phenoxyalkyl carboxylic acids disclosed in U.S. Pat. No. 4,258,058 to Witte et al, especially 4-[2-(benzenesulfamido)ethyl]phenoxyacetic acid, (BM 13,177 - Boehringer Mannheim), the sulphonamidophenyl carboxylic acids disclosed in U.S. Pat. No. 4,443,477 to Witte et al, especially 4-[2-(4-chlorobenzenesulfonamido)ethyl]-phenylacetic acid, (BM 13,505, Boehringer Mannheim) the arylthioalkylphenyl carboxylic acids disclosed in U.S. Pat. No. 4,752,616, especially 4-(3-((4-chlorophenyl)sulfonyl)propyl)benzeneacetic acid.

Other examples of thromboxane $A_2$ antagonists suitable for use herein include, but are not limited to (E)-5-[[[(pyridinyl)[3-(trifluoromethyl)phenyl]methylene]amino]oxy]pentanoic acid also referred to as R68,070 - Janssen Research Laboratories, 3-[1-(4-chlorophenylmethyl)-5-fluoro-3-methylindol-2-yl]-2,2-dimethylpropanoic acid [(L-655240 Merck-Frosst) Eur. J. Pharmacol. 135(2):193, Mar. 17, 1987], 5(Z)-7-([2,4,5-cis]-4-(2-hydroxyphenyl)-2-trifluoromethyl-1,3-dioxan-5-yl)heptenoic acid (ICI 185282, Brit. J. Pharmacol 90 (Proc. Suppl):228 P-Abs., Mar. 87), 5(Z)-7-[2,2-dimethyl-4-phenyl-1,3-dioxan-cis-5-yl]-heptenoic acid (ICI 159995, Brit. J. Pharmacol. 86 (Proc. Suppl):808 P-Abs., Dec. 85), N,N'-bis[7-(3-chlorobenzeneaminosulfonyl)-1,2,3,4-tetrahydro-isoquinolyl]disulfonylimide (SKF 88046, Pharmacologist 25(3):116 Abs, 117 Abs, Aug. 83), [1α(Z)-2β,5α]-(+)-7-[5-[[(1,1'-biphenyl)-4-yl]-methoxy]-2-(4-morpholinyl)-3-oxocyclopentyl]-4-heptenoic acid (AH 23848 - Glaxo, Circulation 72(6):1208, Dec. 85, levallorphan allyl bromide (CM 32,191, Sanofi, Life Sci. 31 (20–21):2261, 15 Nov. 82), (Z,2-endo-3-oxo)-7-(3-acetyl-2-bicyclo-[2.2.1]heptyl-5-hepta-3Z-enoic acid, 4-phenylthiosemicarbazone (EP092 - Univ. Edinburgh, Brit, J. Pharmacol. 84(3):595, Mar. 85).

Examples of thromboxane synthetase inhibitors suitable for use herein include but are not limited to dazoxiben (DZ, Pfizer), imidazole, 1-benzylimidazole, imidazo[1,5-a]pyridine-5-hexanoic acid (CGS 13080), 7-(1-imidazolyl)heptanoic acid (7-IHA), dazmegrel or ozegrel.

The disclosure of the above-mentioned patents, patent applications and other references are incorporated herein by reference.

In carrying out the method of the present invention, calcium channel blocker in combination with the thromboxane $A_2$ receptor antagonist or thromboxane synthetase inhibitor may be administered to mammalian species, such as monkeys, dogs, cats, rats, humans, etc. and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

The dose administered must be carefully adjusted according to age, weight and condition of the patient, as well as the route of administration, dosage form and regimen and the desired result.

Thus, for oral administration, a satisfactory result may be obtained employing the calcium channel blocker in an amount within the range of from about 0.01 mg/kg to about 100 mg/kg and preferably from about 0.1 mg/kg to about 25 mg/kg in combination with the thromboxane $A_2$ receptor antagonist or thromboxane synthetase inhibitor in an amount within the range of from about 0.01 mg/kg to about 100 mg/kg and preferably from about 0.1 mg/kg to about 25 mg/kg with the calcium channel blocker and a thromboxane $A_2$ receptor antagonist or thromboxane synthetase inhibitor being employed together in the same oral dosage form or in separate oral dosage forms taken at the same time.

A preferred oral dosage form, such as tablets or capsules, will contain the calcium channel blocker in an amount of from about 0.1 to about 500 mg, preferably from about 125 to about 200 mg, and more preferably from about 25 to about 150 mg, with the thromboxane $A_2$ receptor antagonist or thromboxane synthetase inhibitor in an amount of from about 1 to about 350 mg, preferably from about 2 to about 200 mg, and more preferably from about 30 to about 150 mg.

For parenteral administration (which are preferred), the calcium channel blocker will be employed in an amount within the range of from about 0.005 mg/kg to about 10 mg/kg and preferably from about 0.01 mg/kg to about 1 mg/kg, with the thromboxane $A_2$ receptor antagonist or thromboxane synthetase inhibitor in an amount within the range of from about 0.005 mg/kg to about 20 mg/kg and preferbly from about 0.01 mg/kg to about 2 mg/kg.

The composition described above may be administered in the dosage forms as described above in single or divided doses of one to four times daily. It may be advisable to start a patient on a low dose combination and work up gradually to a high dose combination.

Tablets of various sizes can be prepared, e.g., of about 50 to 700 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of calcium channel blocker and a thromboxane $A_2$ receptor antagonist or thromboxane synthetase inhibitor are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Many of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for ischemia remains or the symptoms continue. Sustained release forms of such formulations which may provide such amounts biweekly, weekly, monthly and the like may also be employed. A dosing period of at least one to two weeks are required to achieve minimal benefit.

DESCRIPTION OF ACCOMPANYING FIGURES

Figure 2:
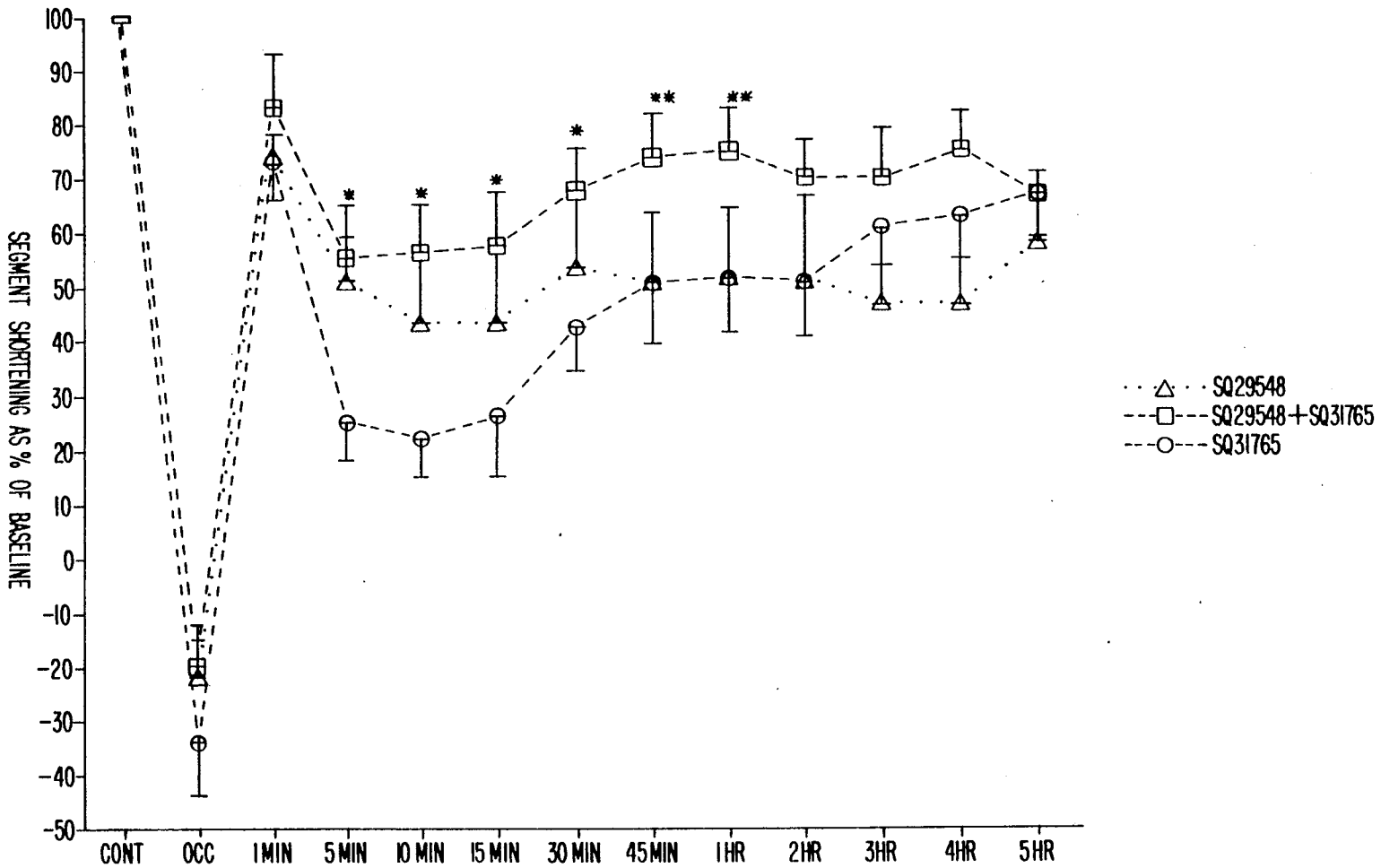

FIG. 1 is a graph showing the effect of SQ 29,548 on recovery of contractile function following a 15 minute LAD occlusion, as described in the experiment carried out in Example 13; and FIG. 2 is a graph showing the effect of SQ 29,548 (n=7) and/or SQ 31,765 (n=6 alone, n=6 combination) on the recovery function following a 15 minute LAD occlusion as described in the experiment carried out in Example 13.

The following Examples represent preferred embodiments of the present invention.

EXAMPLE 1

A thromboxane receptor $A_2$ antagonist-calcium channel blocker formulation suitable for oral administration for treating ischemia and/or reducing myocardial infarct size is set out below.

1000 tablets each containing 400 mg of thromboxane $A_2$ antagonist and 100 mg diltiazem are produced from the following ingredients.

| | |
|---|---|
| [1S-[1β,2α(5Z),3α,4β]]-7-[3-[[[[(1-Oxoheptyl)amino]acetyl]amino]methyl]-7-oxabicyclo[2.2.1]hept-2-yl]-5-heptenoic acid (SQ 30,741) | 400 g |
| Diltiazem | 100 g |
| Corn starch | 50 g |
| Gelatin | 7.5 g |
| Avicel (microcrystalline cellulose) | 25 g |
| Magnesium stearate | 2.5 g |

The thromboxane antagonist, diltiazem and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 500 mg of active ingredients.

EXAMPLES 2 AND 3

The following aerosol formulations may be used in treating ischemia and/or reducing myocardial infarct size.

| Example 2 | | Amount % by Wt. | Specific Amount % by Wt. |
|---|---|---|---|
| SQ 30,471 | | 0.01 to 1 | 0.05 |
| Nifedipine | | 0.01 to 1 | 0.05 |
| Ethanol | | 5–50 | 25 |
| Freon 11 or 114 / Freon 12 | 50–50 mixture | 50–95 | 74.95 |

| Example 3 | | % by Wt. |
|---|---|---|
| SQ 30,741 | | 0.01–1 |
| Verapamil | | 0.01–1 |
| Surfactant (Oleic acid, oleyl alcohol, lecithin) | | qs. |
| Water | | qs. |
| Freon 11 or 114 / Freon 12 | 50–50 mixture | qs. to 100% |

EXAMPLE 4

An injectable solution for use in administering calcium channel blocker and thromboxane $A_2$ receptor antagonist is produced as follows:

| | |
|---|---|
| [1S-[1α,2β(5Z),3β,4α]]-7-[3-[[2-(phenylamino)carbonyl]hydrazino]-methyl]-7-oxabicyclo[2.2.1]hept-2-yl]-5-heptenoic acid (SQ 29,548) or SQ 30,741 | 2500 mg |
| Nifedipine or diltiazem | 2500 mg |
| Methyl paraben | 5 mg |
| Propyl paraben | 1 mg |
| Sodium chloride | 25 g |
| Water for injection qs. | 5 l. |

The calcium channel blocker, thromboxane $A_2$ antagonist, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains a concentration of 75 mg of active ingredient per 150 ml of solution.

EXAMPLE 5

An injectable for use in treating ischemia and/or reducing myocardial infarct size is prepared as described in Example 4 except that the thromboxane $A_2$ antagonist employed is the phenoxyalkyl carboxylic acid 4-[2-(benzenesulfamido)ethyl]phenoxyacetic acid, disclosed in U.S. Pat. No. 4,258,058.

EXAMPLE 6

An injectable for use in treating ischemia is prepared as described in Example 4 except that the thromboxane $A_2$ antagonist employed is [1S-[1α,2β(Z),3β,4α]]-7-[3-[[[[(4-cyclohexyl-1-oxobutyl)amino]acetyl]amino]methyl]-7-oxabicyclo-[2.2.1]hept-2-yl]-5-heptenoic acid.

EXAMPLE 7

1000 tablets each containing 200 mg of SQ 32,324 and 400 mg SQ 30,741 are produced from the following ingredients:

| | |
|---|---|
| (d-cis)-3-(acetyloxy)-1,3,4,5-tetrahydro-4-(4-methoxyphenyl)-1-[2-(methylamino)ethyl]-6-(trifluoromethyl)-2H-1-benzazepin-2-one, monohydrochloride salt (SQ 32,324) | 200 g |
| SQ 30,741 | 400 g |
| Lactose | 100 g |
| Avicel | 150 g |
| Corn starch | 50 g |
| Magnesium stearate | 5 g |

SQ 32,324, SQ 30,741, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in treating ischemia and/or reducing myocardial infarct size.

EXAMPLE 8

Two piece #1 gelatin capsules each containing 250 mg of diltiazem and 250 mg of SQ 30,741 are filled with a mixture of the following ingredients:

| | |
|---|---|
| SQ 30,741 | 250 mg |
| Diltiazem | 250 mg |
| Magnesium stearate | 7 mg |
| USP lactose | 193 mg. |

The resulting capsules are useful in treating ischemia.

EXAMPLE 9

An injectable solution for use in treating ischemia and/or reducing myocardial infarct size is produced as follows:

| | |
|---|---|
| (d-cis)-3-(acetyloxy)-1-[2-dimethylamino)ethyl]-1,3,4,5-tetrahydro-4-(4-methoxyphenyl)-6-(trifluoromethyl)-2H-1-benzazepin-2-one, monohydrochloride (SQ 31,765) | 500 mg |
| SQ 30,741 | 250 mg |
| Methyl paraben | 5 mg |
| Propyl paraben | 1 mg |
| Sodium chloride | 25 g |
| Water for injection qs. | 5 l. |

SQ 31,765, SQ 30,741, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

EXAMPLE 10

A thromboxane synthetase inhibitor-calcium channel blocker formulation suitable for oral administration for treating ischemia and/or reducing myocardial infarct size prepared as described in Example 1, is set out below.

1000 tablets each containing 400 mg of thromboxane synthetase inhibitor and 100 mg diltiazem are produced from the following ingredients.

| | |
|---|---|
| Dazoxiben | 400 g |
| Diltiazem | 100 f |

-continued

| | |
|---|---|
| Corn starch | 50 g |
| Gelatin | 7.5 g |
| Avicel (microcrystalline cellulose) | 25 g |
| Magnesium stearate | 2.5 g |

EXAMPLE 11

An injectable solution for use in administering calcium channel blocker and thromboxane synthetase inhibitor, produced as described in Example 4, has the following composition.

| | |
|---|---|
| Imidazole or 1-benzylimidazole | 2500 mg |
| Nifedipine or diltiazem | 2500 mg |
| Methyl paraben | 5 mg |
| Propyl paraben | 1 mg |
| Sodium chloride | 25 g |
| Water for injection qs. | 5 l. |

EXAMPLE 12

An injectable for use in treating ischemia and/or reducing myocardial infarct size is prepared as described in Example 4 except that the thromboxane synthetase inhibitor employed is imidazo[1,5-a]pyridine-5-hexanoic acid (CGS 13080).

EXAMPLE 13

The following experiments were carried out to demonstrate the use of the combination of the thromboxane $A_2$ receptor antagonist SQ 29,548 and the calcium channel blocker SQ 31,765 in treating myocardial ischemia.

As described previously (Weiner, J. M. et al., Cardiovasc. Res. 10:678, 1976), some degree of contractile dysfunction or "stunning" usually persists following a coronary occlusion of short duration even if no significant necrosis occurs. Not much is known about the mechanism of this dysfunction, though some aspects of "reperfusion injury" such as activated inflammatory response can play a role (Myers, M. L., et al., Circulation 72:915, 1985). It has been found that a calcium channel blocker, SQ 31,765, is capable of improving the recovery of post-ischemic contractile dysfunction. Calcium channel blockers have not been found to be effective during the reperfusion period in other ischemia models and thus the protective effect of SQ 31,765 is most likely to be taking place during the coronary occlusive event (Klein, H. H., Circulation 69:1000, 1984).

The role of thromboxane $A_2$ (TXA) in contributing to this myocardial stunning has not been previously examined. TXA is released during ischemia and particularly during reperfusion (Tanabe, M., et al., Cardiovasc. Res. 16;99, 1987); thus it may play a role in exacerbating the myocardial stunning evident after a short-term occlusion. One means of studying this question would be to use a selective TXA receptor antagonist which has the advantage of abolishing TXA mediated events without altering the production of arachidonic acid metabolites from parallel synthetic pathways (Bertele, V., et al., Blood 63:1460, 1984). Thus, the first goal of the present study was to determine if the selective TXA/endoperoxide receptor antagonist, SQ 29,548, can result in an enhanced recovery of contractile function following an acute coronary occlusion of insufficient severity to result in myocardial infarction.

If TXA antagonists are found to be efficacious in this model of stunned myocardium, it would be of interest to know if they ct via the same mechanism as calcium channel blockers. If they work via separate mechanisms, the possibility exists for successful combination therapy. Such a combination may be useful as coronary disease of multiple or unknown etiology may be better treated. This is especially attractive since the TXA antagonists seem to be hemodynamically innocuous in normotensive animals and there should not be any additional adverse side effects such as hypotension or tachycardia for this additional protective effect. Many combination therapies for coronary disease (such as calcium and $\beta$-blockers) have added risks because the compounds have similar actions or mechanisms of action which when multiplied (due to combination therapy) may become important side effects (e.g., excessive cardiac depression or hypotension). Thus, the second goal of the present study was to determine if calcium and TXA antagonists can reduce the severity of myocardial stunning via separate mechanisms or at least not have a deleterious effect when combined. To this end, it was determined if SQ 31,765 can further enhance functional recovery following an acute coronary occlusion when superimposed on a dose of SQ 29,548 that results in virtually complete TXA receptor blockade.

Methods

Adult mongrel dogs (10–15 kg) were anesthesized using pentobarbital sodium (30 mg/kg, i.v.). Aortic blood pressure was measured using a Mikro-Tip catheter transducer (Millar Instruments) inserted into the right carotid artery. The right femoral artery was catheterized for collection of blood for measurement of blood gases. A left femoral venous catheter was inserted for drug infusion and supplemental anesthesia.

Each animal was intubated and placed on artificial respiration such that eucapnia was maintained. They were then subjected to a left thoracotomy and the pericardium was formed into a cradle. The left anterior descending coronary artery was isolated proximal to its first branch and a silk ligature was placed around it. A left atrial catheter was implanted for injection of dye (determining the area at risk) at the end of the experiment. Regional function was determined using ultrasonic crystals implanted into the subendocardium of the left anterior descending artery (LAD) (soon to be ischemic) perfused region. The crystals in each pair were placed approximately 10 mm apart. Baseline blood pressure, heart rate, and segment shortening were recorded once the animals had equilibrated.

At this time, the animals were divided into groups: 1. Animals given i.v. SQ 29,548 (0.20 mg/kg+0.20 mg/kg/hr, n=7); 2. Animals given i.v. SQ 29,548 (0.20 mg/kg+0.20 mg/kg/hr)+SQ 31,765 (20 mg/kg n=6); 3. Animals given i.v saline (4–5 ml, n=9). Fifteen minutes after the onset of drug injection, hemodynamic and shortening variables were again determined and the LAD was completely occluded for 15 minutes. The occlusion was released and the reperfusion was allowed to continue for an additional 5 hours. Hemodynamic and segment shortening data were collected during the LAD occlusion and at intervals throughout the reperfusion period. At the end of the experiment, the area at risk was determined, as described previously, by injection of patent blue violet dye into the left atrial catheter while the LAD was being perfused with Ringer's lactate at the animals existing arterial blood pressure. The hearts were then removed and the area at risk was determined.

The segment shortening data were normalized as previously described by Theroux et al (Circulation 53:302,1976) and Shimshak et al. (Cardiovasc. Res. 20:621, 1986). End diastolic length (EDL) was determined at the onset of left ventricular isovolumetric contraction and end systolic length (ESL) was determined at maximum $-dp/dt$. The percentage segment shortening (% SS) was calculated from the equation: % SS=(EDL−ESL)/EDL.

All data are presented as mean ±SE. Between treatment, hemodynamic comparisons were made using a one-way analysis of variance and multiple comparisons were determined using the Neuman-Keuls test. Segment shortening was expressed as a percent of initial baseline values and between treatment comparisons were made using the Kruskal-Wallis test for nonparametric data. A value of $P<0.05$ was accepted as significant.

Results

Hemodynamic data for all groups are shown on Table 1. Arterial blood pressure was relatively constant throughout the course of the experiment for all groups. Baseline heart rate tended to be lower in the group of animals to be treated with both SQ 31,765+SQ 29,548 though this was not significantly different when compared to the saline-treated control group. The combination treatment resulted in a slight decrease in heart rate that was not significantly different compared to their paired baseline values. Blood gases were held within a normal physiological range throughout the experiment.

Segmental shortening data for the subendocardial LAD region in animals treated with saline or SQ 29,548 are shown in FIG. 1. LAD occlusion resulted in significant systolic bulging in the occluded region for both drug-treated and saline-treated animals. Immediately upon reperfusion, segment shortening returned towards baseline values for both groups. By 5 minutes, however, shortening started declining again in both groups, though to a lesser extent in SQ 29,548-treated animals. SQ 29,548 resulted in significantly higher segmental function throughout most of the reperfusion period measured during this experiment. At the end of the experiment (5 hours post-reperfusion), segmental shortening returned to levels approximately 25% of baseline values in saline-treated animals compared to 60% in animals treated with SQ 29,548. The effect of combination treatment with both SQ 29,548 and SQ 31,765 on segmental shortening following coronary occlusion is shown on FIG. 2. Though the values for saline-treated animals are not shown in this figure, treatment with SQ 29,548 or SQ 31,765 alone resulted in significant improvements in contractile function during reperfusion compared to saline-treated animals at most of the times measured. SQ 29,548 seemed to result in an earlier return of function compared to SQ 31,765 and the significance of this, if any, is presently unknown. Treatment with both of these compounds simultaneously also resulted in significant improvement in segmental shortening at nearly all reperfusion time points chosen compared to saline-treated controls. Combination treatment resulted in a significantly higher reperfusion function at 5-30 minutes compared to values for SQ 31,765-treated animals. Combination treatment resulted in an improved functional status compared to the SQ 31,765 and SQ 29,548-treated groups at 45 minutes and 1 hour post-reperfusion. No other differences were noted.

Discussion

There is presently a great deal of interest in studies concerning the loss of contractile function following a short-term, temporary coronary occlusion. Little is known about the precise mechanism by which this hypokinesia is occurring, but it is felt that such a phenomenon may have important implications in some clinical settings (Shimsahk, T. M., et al., Cardiovasc. Res. 20:621, 1986). Thromboxane (TXA) is thought to play a deleterious role in many types of myocardial ischemia though its exact role is still vague. Previous to the present study, it was unknown if TXA was implicated in the loss of contractile function or "stunning" observed after brief coronary occlusions. Few studies on the role of TXA in ischemic models of relatively low severity have been performed and the results of these few studies have been mixed (DeBono, P., et al., Br. Heart J., 56:509, 1986; Ito, T., et al., J. Mol. Cell Cardiol. 19 (Suppl I) S12, 1987). Thus, the first goal of this study was to determine if the selective TXA receptor antagonist, SQ 29,548, could enhance the recovery of contractile function following a 15 minute LAD occlusion and thereby implicate a role for TXA in this clinically relevant model.

The TXA receptor antagonist, SQ 29,548, was found to significantly enhance recovery of function in the ischemic subendocardial region. This indicates a role for TXA in mediating some aspects of myocardial stunning. It is known that TXA is released during coronary occlusions of short duration, though the effect of this release is still under debate. It is not known if the beneficial effect of SQ 29,548 was due to its action during the coronary occlusion or during the reperfusion. It has been shown that SQ 29,548 can exert a beneficial effect during a coronary occlusion, though this does not exclude the possibility of a beneficial effect during the reperfusion.

As shown, the dose of SQ 29,548 used in the present study results in a virtually complete TXA receptor blockade. With this knowledge, it becomes possible to determine if other classes of anti-ischemic agents can act through independent mechanisms. TXA antagonists and calcium antagonists reduce the severity of myocardial ischemia through different mechanisms. Thus, these two classes of compounds acting through different mechanisms may be combined to treat heart disease of multiple or unknown etiology, without the disadvantages of combining compounds working via similar mechanisms (e.g., cardiodepression with $\beta$-adrenoceptor antagonists and calcium antagonists). Thus, there was interest in determining if SQ 29,548 and SQ 31,765 could enhance functional recovery of stunned myocardial tissue in an additive fashion.

It has been found that SQ 31,765 significantly reduced the degree of stunning found following reperfusion of a formerly occluded region. When the combination of SQ 29,548 and SQ 31,765 were administered simultaneously, despite virtually complete TXA receptor blockade, SQ 31,765 resulted in a further slight though statistically significant improvement in function. This suggests that these compounds may be working in part via separate mechanisms. The other important observation was that the combination of these two compounds did not seem to result in any noticeable deleterious hemodynamic effects. This may be of importance as combination treatment may result in wider coverage of coronary disease of multiple etiology or enhance the beneficial effects for a given etiology, but without paying a significant price in terms of added negative effects.

TABLE 1

The effect of SQ 29,548 or SQ 31,765 on Hemodynamic Variables During LAD Occlusion and Reperfusion

| | Pre Drug | Post-Drug | LAD Occlusion (15 min) | Time Post-Reperfusion 1 min | 10 min | 30 min | 1 hr | 5 hr |
|---|---|---|---|---|---|---|---|---|
| Systolic Blood Pressure (mmHg) | | | | | | | | |
| Saline (n = 7) | 118 ± 6 | 113 ± 6 | 113 ± 6 | 109 ± 6 | 113 ± 4 | 120 ± 4 | 120 ± 4 | 123 ± 4 |
| SQ 29,548 (n = 7) | 109 ± 5 | 108 ± 5 | 106 ± 6 | 106 ± 6 | 105 ± 5 | 107 ± 5 | 111 ± 5 | 109 ± 6 |
| SQ 29,548 + SQ 31,765 (n = 6) | 100 ± 8 | 95 ± 9 | 94 ± 8 | 98 ± 8 | 99 ± 9 | 101 ± 9 | 104 ± 8 | 108 ± 5 |
| Diastolic Blood Pressure (mmHg) | | | | | | | | |
| Saline (n = 7) | 92 ± 5 | 94 ± 5 | 89 ± 5 | 85 ± 6 | 84 ± 3 | 88 ± 4 | 91 ± 3 | 92 ± 3 |
| SQ 29,548 (n = 7) | 88 ± 4 | 86 ± 4 | 83 ± 5 | 82 ± 4 | 83 ± 4 | 83 ± 4 | 86 ± 4 | 80 ± 4 |
| SQ 29,548 + SQ 31,765 (n = 6) | 76 ± 7 | 70 ± 7 | 70 ± 7 | 72 ± 7 | 72 ± 8 | 75 ± 7 | 78 ± 8 | 80 ± 5 |
| Heart Rate (beats/min) | | | | | | | | |
| Saline (n = 7) | 157 ± 5 | 156 ± 4 | 157 ± 4 | 148 ± 5 | 155 ± 3 | 158 ± 4 | 158 ± 4 | 159 ± 3 |
| SQ 29,548 (n = 7) | 155 ± 7 | 154 ± 6 | 157 ± 7 | 152 ± 7 | 156 ± 6 | 156 ± 6 | 157 ± 5 | 161 ± 6 |
| SQ 29,548 + SQ 31,765 | 140 ± 5 | 131 ± 4[a] | 134 ± 5[a] | 135 ± 5 | 139 ± 5[a] | 142 ± 6 | 140 ± 8 | 162 ± 9 |

All values are mean ± SE

[a]Significantly different compared to saline-treated animals ($p < 0.05$)

What is claimed is:

1. A method for treating ischemia and/or reducing myocardial infarct size in a mammalian specie, which comprises administering to a mammalian specie in need of such treatment an effective amount of a combination of a calcium channel blocker and a thromboxane $A_2$ receptor antagonist employed in a weight ratio to each other of from about 0.1:1 to about 10:1.

2. The method as defined in claim 1, wherein the calcium channel blocker is diltiazem, nifedipine, nitrendipine, verapamil or tiapamil.

3. The method as defined in claim 1, wherein the thromboxane $A_2$ antagonist has the name [1S-[1α,2β(5Z),3β(1E,3R,4S),4α]]-7-[3-(3-hydroxy-4-phenyl-1-pentenyl)-7-oxabicyclo[2.2.1]hept-2-yl]-5-heptenoic acid; [1S-[1α,2β(5Z),3α,4β]]-7-[3-[[[[(1-oxoheptyl)amino]acetyl]amino]methyl]-7-oxabicyclo[2.2.1]-hept-2-yl]-5-heptenoic acid or the corresponding tetrazole; [1S-[1α,2β(Z),3β,4α]]-7-[3-[[[[(4-cyclohexyl-1-oxobutyl)amino]acetyl]amino]methyl]-7-oxabicyclo-[2.2.1]hept-2-yl]-5-heptenoic acid; [1S-[1α,2β(5Z),3β,-4α]]-7-[3-[2-(phenylamino)carbonyl]hydrazino]methyl]-7-oxabicyclo[2.2.1]hept-2-yl]-5-heptenoic acid, 4-(3-((4-chlorophenyl)sulfonyl)propyl)benzene acetic acid; 4-[2-(4-chlorobenzenesulfonamido)ethyl]phenylacetic acid.

4. The method as defined in claim 1 wherein a calcium channel blocker in combination with said thromboxane $A_2$ receptor antagonist is administered orally or parenterally.

5. The method as defined in claim 1 wherein said calcium channel blocker is diltiazem, (d-cis)-3-(acetyloxy)-1-[2-dimethylamino)ethyl]-1,3,4,5-tetrahydro-4-(4-methoxyphenyl)-6-(trifluoromethyl)-2H-1-benzazepin-2-one, monohydrochloride (SQ 31,765) or (d-cis)-3-(acetyloxy)-1,3,4,5-tetrahydro-4-(4-methoxyphenyl)-1-[2-(methylamino)ethyl]-6-(trifluoromethyl)-2H-1-benzazepin-2-one, monohydrochloride salt (SQ 32,324) and is administered systemically in an amount of from about 0.1 to about 500 mg/1 to 4 times a day and said thromboxane $A_2$ receptor antagonist is SQ 30,741 and is administered systemically in an amount of from about 0.1 to about 500 mg/1 to 4 times a day.

6. A combination useful for treating ischemia comprising a calcium channel blocker and a thromboxane $A_2$ receptor antagonist employed in a weight ratio to each other from about 0.1:1 to about 10:1.

7. The combination as defined in claim 6 wherein the calcium channel blocker is employed in a weight ratio to the thromboxane $A_2$ receptor antagonist of within the range of from about 0.4:1 to about 2.5:1.

8. The method as defined in claim 1 wherein the thromboxane $A_2$ receptor antagonist is a 7-oxabicycloheptane substituted diamide prostaglandin analog.

9. The method as defined in claim 8 wherein the calcium channel blocker is diltiazem and the thromboxane $A_2$ receptor antagonist is [1S-[1α,2β(5Z),3α,4β]]-7-[3-[[[[(1-oxoheptyl)amino]acetyl]amino]methyl]-7-oxabicyclo[2.2.1]-hept-2-yl]-5-heptenoic acid.

10. The method as defined in claim 10 wherein the thromboxane $A_2$ receptor antagonist is a 7-oxabicycloheptane substituted diamide prostaglandin analog.

11. The combination as defined in claim 10, wherein the calcium channel blocker is diltiazem and the thromboxane $A_2$ receptor antagonist is [1S-[1β,2α(5Z)-,3α,4β]]-7-[3-[[[[(1-oxoheptyl)amino]acetyl]amino]methyl]-7-oxabicyclo[2.2.1]-hept-2-yl]-5-heptenoic acid.

* * * * *